United States Patent
Walsh (10) Patent No.: US 10,302,733 B2
(45) Date of Patent: May 28, 2019

(54) NMR SPIN-ECHO AMPLITUDE ESTIMATION

(71) Applicant: VISTA CLARA INC., Mukilteo, WA (US)

(72) Inventor: David O. Walsh, Mukilteo, WA (US)

(73) Assignee: VISTA CLARA INC., Mukilteo, WA (US)

( * ) Notice: Subject to any disclaimer, the term of this patent is extended or adjusted under 35 U.S.C. 154(b) by 108 days.

(21) Appl. No.: 15/383,840

(22) Filed: Dec. 19, 2016

(65) Prior Publication Data

US 2017/0219675 A1   Aug. 3, 2017

Related U.S. Application Data

(60) Provisional application No. 62/269,021, filed on Dec. 17, 2015.

(51) Int. Cl.
| | |
|---|---|
| *G01V 3/00* | (2006.01) |
| *G01R 33/58* | (2006.01) |
| *G01R 33/44* | (2006.01) |
| *G01R 33/46* | (2006.01) |
| *G01N 24/08* | (2006.01) |

(52) U.S. Cl.
CPC ......... *G01R 33/583* (2013.01); *G01N 24/081* (2013.01); *G01R 33/441* (2013.01); *G01R 33/4625* (2013.01); *G01R 33/448* (2013.01)

(58) Field of Classification Search
CPC ........ G01N 24/081; G01N 24/08; G01V 3/32; G01R 33/5617; G01R 33/448; G01R 33/3808; G01R 33/445; G01R 33/302; G01R 33/34007; G01R 33/341; G01R 33/383; G01R 33/443; G01R 33/46

USPC .......................................................... 324/309
See application file for complete search history.

(56) References Cited

U.S. PATENT DOCUMENTS

| | | | | |
|---|---|---|---|---|
| 2005/0248342 | A1* | 11/2005 | Rottengatter | G01V 3/32 324/303 |
| 2006/0273787 | A1* | 12/2006 | Blanz | G01N 24/081 324/303 |
| 2007/0290126 | A1* | 12/2007 | Kurkoski | G01T 1/171 250/262 |
| 2008/0024128 | A1* | 1/2008 | Song | G01N 24/081 324/307 |

(Continued)

OTHER PUBLICATIONS

Anand and Hirasaki, "Paramagnetic relaxation in sandstones: Distinguishing T1 and T2 dependence on surface relaxation, internal gradients and dependence on echo spacing", Article, Journal of Magnetic Resonance, Oct. 2007.

*Primary Examiner* — Rodney E Fuller
(74) *Attorney, Agent, or Firm* — Nathaniel A. Gilder (57) ABSTRACT

Technologies applicable to NMR spin-echo amplitude estimation are disclosed. Example methods may calibrate for distortion of a shape and estimated amplitude of measured NMR spin or gradient echoes. NMR spin or gradient echo measurements may be performed on a sample. The measured NMR spin or gradient echoes may be used to calculate an echo-shape calibration factor. The echo-shape calibration factor may estimate an effect of echo shape on estimated spin or gradient echo amplitude(s) of the NMR spin or gradient echoes. The echo-shape calibration factor may be used to correct for underestimation or overestimation of the spin or gradient echo amplitude(s).

20 Claims, 3 Drawing Sheets

(56) References Cited

U.S. PATENT DOCUMENTS

| | | | |
|---|---|---|---|
| 2012/0235677 A1* | 9/2012 | Blanz | G01N 24/081 324/303 |
| 2013/0162247 A1* | 6/2013 | Hurlimann | G01N 24/081 324/303 |
| 2015/0060054 A1* | 3/2015 | Bordoloi | E21B 43/00 166/250.01 |
| 2016/0077183 A1* | 3/2016 | Jachmann | G01R 33/586 324/314 |
| 2016/0116629 A1* | 4/2016 | Coman | G01V 3/32 324/303 |
| 2016/0327626 A1* | 11/2016 | Ha | G01R 33/46 |
| 2017/0102345 A1* | 4/2017 | Lei | G01N 24/08 |
| 2017/0212063 A1* | 7/2017 | Kantzas | G01N 24/081 |
| 2017/0315199 A1* | 11/2017 | Heaton | G01R 33/5608 |

\* cited by examiner

NMR SPIN-ECHO AMPLITUDE ESTIMATION

CROSS-REFERENCE TO RELATED APPLICATIONS

This is a nonprovisional claiming priority under 35 U.S.C. § 119 of co-pending U.S. Provisional Patent Application No. 62/269,021, entitled "NMR SPIN-ECHO AMPLITUDE ESTIMATION", filed on Dec. 17, 2015. The prior application is incorporated by reference herein in its entirety.

STATEMENT OF GOVERNMENT SUPPORT

This invention was made in part with Government support under Agreements DE-SC0006376 and DE-SC0011387 awarded by the US Department of Energy. The Government has certain rights in this invention.

BACKGROUND

NMR data processing may involve averaging over a finite window of measured samples, centered over the expected peak of each spin echo, to estimate the amplitudes of individual spin echoes. The result of this averaging procedure is dependent on the shape of the echo. For example, if the echo amplitude and phase are perfectly constant over the duration of the averaging window the calculated average will provide an accurate estimate of the peak echo amplitude. If however, the amplitude and/or phase of the echo changes significantly over the averaging window, then the calculated average will significantly underestimate the peak echo amplitude. This underestimation effect can be expected when using a rectangular averaging window or a time-domain-weighted averaging function such as a Hanning window.

The time domain shape of a spin echo may be controlled by the distribution of static magnetic field gradients across the spin-density volume of the sample under investigation. If the static magnetic field exhibits smaller gradients across the sample of interest, the echo shape tends to be generally broader and flatter across the fixed length time domain averaging window. If the static magnetic field exhibits larger gradients across the same sample of interest, the echo shape tends to be generally narrower with more rapid dephasing on either side of the echo peak. In addition some NMR measurement effects can cause the echo peak to shift in time, and this can also affect the time domain average as calculated over a fixed echo averaging window.

Figure 1:
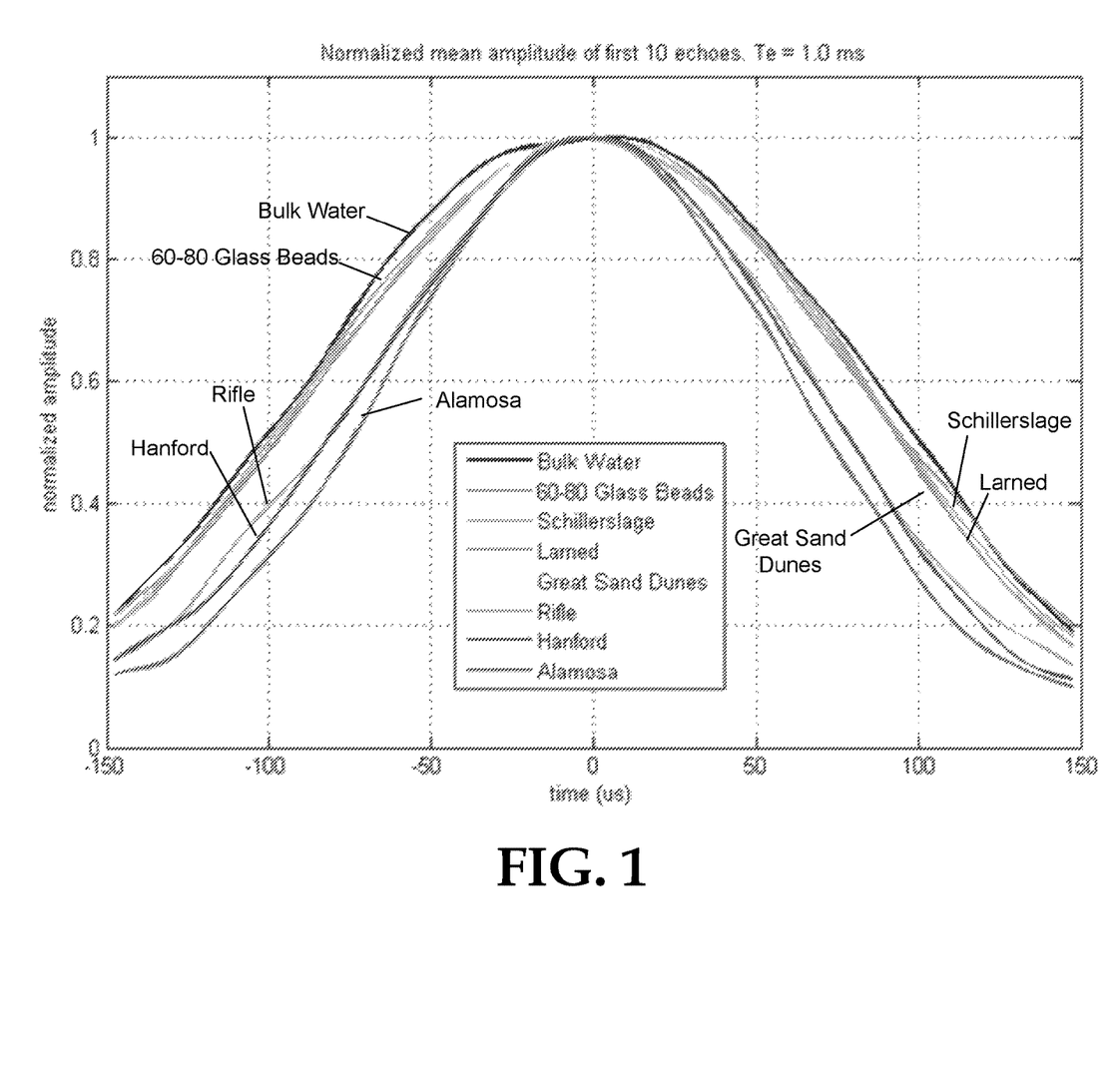
FIG. 1 illustrates an example comparison of measured NMR spin echo shapes for bulk water and water-saturated soil samples with different bulk magnetic susceptibilities.

In many practical applications the magnetic field gradients across a sample of interest are unknown and outside the control of the NMR measurement device or the user. For example, naturally-occurring soil and rock samples often have significant magnetic mineral content, and this content can induce significant gradients in the static magnetic field of the measurement device across and within the volume of the sample under investigation. For applications involving detection of water, oil or other hydrogen-rich fluids these internal sample-induced gradients cause the NMR resonance frequency (the Larmor frequency) of the fluids to vary significantly within the sample volume, and this causes a sharpening of the echo shape. An example of this effect is shown in FIG. 1, which compares the measured NMR spin echo shapes for bulk water and seven water-saturated soil samples with different bulk magnetic susceptibilities. These samples were all measured under identical conditions in the same 275 kHz laboratory spectrometer. The samples with relatively high bulk magnetic susceptibility (Labeled "Rifle", "Hanford" and "Alamosa") exhibit significantly sharper and narrower echo shapes than the other samples that have lower bulk magnetic susceptibility. This effect can occur for laboratory NMR spectrometers which are designed to have low gradients, for NMR logging tools that often have high gradients, and also for surface NMR instruments that perform NMR measurements in the Earth's magnetic field. These internal gradient effects can also affect medical magnetic resonance imaging measurements, in particular in and around volumes of tissue or objects that induce magnetic susceptibility contrasts.

For some NMR measurement devices, the NMR amplitude response of the device may be calibrated under some known, nominal measurement condition. For example, with a laboratory NMR spectrometer, one can calibrate the NMR amplitude response for a known sample of bulk water or some other fluid or solid. Or for example, one can calibrate the NMR amplitude response of an NMR logging tool by immersing the tool in a volume of water or other fluid or solid that is known to incorporate the entire NMR sensitive volume of the tool. In such calibration schemes, the peak echo amplitude may be estimated for each echo by averaging the recorded data over a finite window of samples centered on the location of the expect peak of each echo. Hence, these commonly-performed calibration methods do not account for the distortions of the spin echo shape that are caused by unknown internally-induced or externally-applied magnetic field gradients in actual sample measurement conditions. And thus, these actual sample measurement conditions, coupled with windowing and time-averaging methods, often result in under-estimation of actual measured echo amplitudes. This in turn leads to underestimation of the underlying spin density, and in particular this can lead to underestimation of sample fluid content.

SUMMARY

Technologies applicable to NMR spin-echo amplitude estimation are disclosed. Some example methods may comprise calibrating for distortion of a shape and estimated amplitude of one or more recorded NMR spin or gradient echoes. The distortion may be caused, for example, by changes in a magnetic field gradient across or within a sample of investigation. Methods may include performing NMR spin or gradient echo measurements on the sample in order to record the one or more NMR spin or gradient echoes. The one or more NMR spin or gradient echo measurements may resolve a time domain shape of the recorded NMR spin or gradient echoes. Methods may furthermore use the recorded NMR spin or gradient echoes to calculate an echo-shape calibration factor. The echo-shape calibration factor may estimate an effect of echo shape on estimated spin or gradient echo amplitude(s) of the recorded NMR spin or gradient echoes. Methods may furthermore use the echo-shape calibration factor to correct for underestimation or overestimation of the spin or gradient echo amplitude(s).

Some example methods may include a measurement control unit configured to perform the NMR spin or gradient echo measurements on the sample in order to record the NMR spin or gradient echoes. A data processing unit may then use the recorded NMR spin or gradient echoes to calculate an echo-shape calibration factor, and use the echo-shape calibration factor to correct for underestimation or overestimation of the spin or gradient echo amplitude(s). Further aspects of the disclosure are described herein.

DETAILED DESCRIPTION

Prior to explaining embodiments of the invention in detail, it is to be understood that the invention is not limited to the details of construction or arrangements of the components and method steps set forth in the following description or illustrated in the drawings. The invention is capable of other embodiments and of being practiced and carried out in various ways. Also, it is to be understood that the phraseology and terminology employed herein are for the purpose of the description and should not be regarded as limiting.

Technologies directed to NMR spin-echo amplitude estimation are disclosed. In one embodiment, an echo-shape correction factor may be estimated as a ratio of a peak measured or estimated amplitude of an echo in an NMR sample measurement, divided by a time-windowed average of the echo within a time-averaging window. Spin echo amplitudes estimated by time-domain averaging may then be multiplied by this correction factor to correct for the effect of the echo shape.

In another embodiment, an optional background measurement of the spin echo shape may be normalized to have unit peak amplitude, and a sample measurement of the spin echo shape may also be normalized to have unit peak amplitude. The echo shape correction factor may then be calculated as a ratio of the time-windowed average of the normalized background measurement, divided by the time-windowed average of the normalized sample measurement. The echo-shape calibration factor may then be applied to the sample NMR measurement to correct for errors in the estimated echo amplitudes due to unknown external or internal magnetic field gradients across the sample. This embodiment enables the background measurement to be used as a measurement calibration for spin density under known conditions (i.e. for calibrating the NMR amplitude response for 100% volumetric bulk water), while the echo-shape calibration procedure corrects for differences in the time-windowed-averages of echo amplitudes that are caused by differences in the shapes of the echoes under the background and sample measurement conditions.

In another embodiment, the echo shape(s) in the sample and optional background conditions may be estimated by averaging multiple time-offset spin echoes in order to reduce the noise on the estimate of the echo shape function. For example, in a Carr-Purcell-Meiboom-Gill (CPMG) measurement that acquires 10 or more echoes in a single scan, the average echo shape can be estimated by averaging the first 10 echoes together, to provide a composite "mean echo shape" with higher signal to noise than the first echo alone.

In another embodiment, the disclosed method may be used to correct for NMR echo shape variations on fluid content measurements of fluid-saturated samples investigated using an NMR spectrometer. In this embodiment, the disclosed method may be used to calibrate for the different echo shapes that are induced and measured between NMR measurements of bulk fluids and NMR measurements of fluid-saturated porous materials.

In another embodiment, the disclosed method may be used to calibrate for the effect of magnetically susceptible earth formations on NMR estimates of volumetric fluid content within said earth formations. In one such embodiment, the NMR sample measurements are performed on earth core or soil samples in a NMR spectrometer, and optional background calibration measurements are performed in the same NMR spectrometer using samples of bulk fluids such as water or oil. In another such embodiment, the NMR sample measurements are performed within earth boreholes using an NMR logging tool, and optional background calibration measurements are performed using the same NMR or similar logging tool to measure the NMR response of bulk fluids such as water or oil. In another such embodiment, the sample NMR measurements are performed using an earth's field surface NMR instrument, and the echo shape calibration factor(s) are used to correct the estimates of spin echo amplitudes that are used for water content and relaxation time estimates.

In another embodiment, the disclosed method may be used to correct for magnetic susceptibility effects in medical MRI images.

In some embodiments, any of the various methods disclosed herein may be carried out by a computing device. Computing devices comprising appropriate hardware, and computer readable media comprising appropriate instructions to carry out the methods described herein are expressly contemplated. This includes, e.g., NMR measurement acquisition hardware, signal processing software, and any subsequent data processing software.

Figure 2:
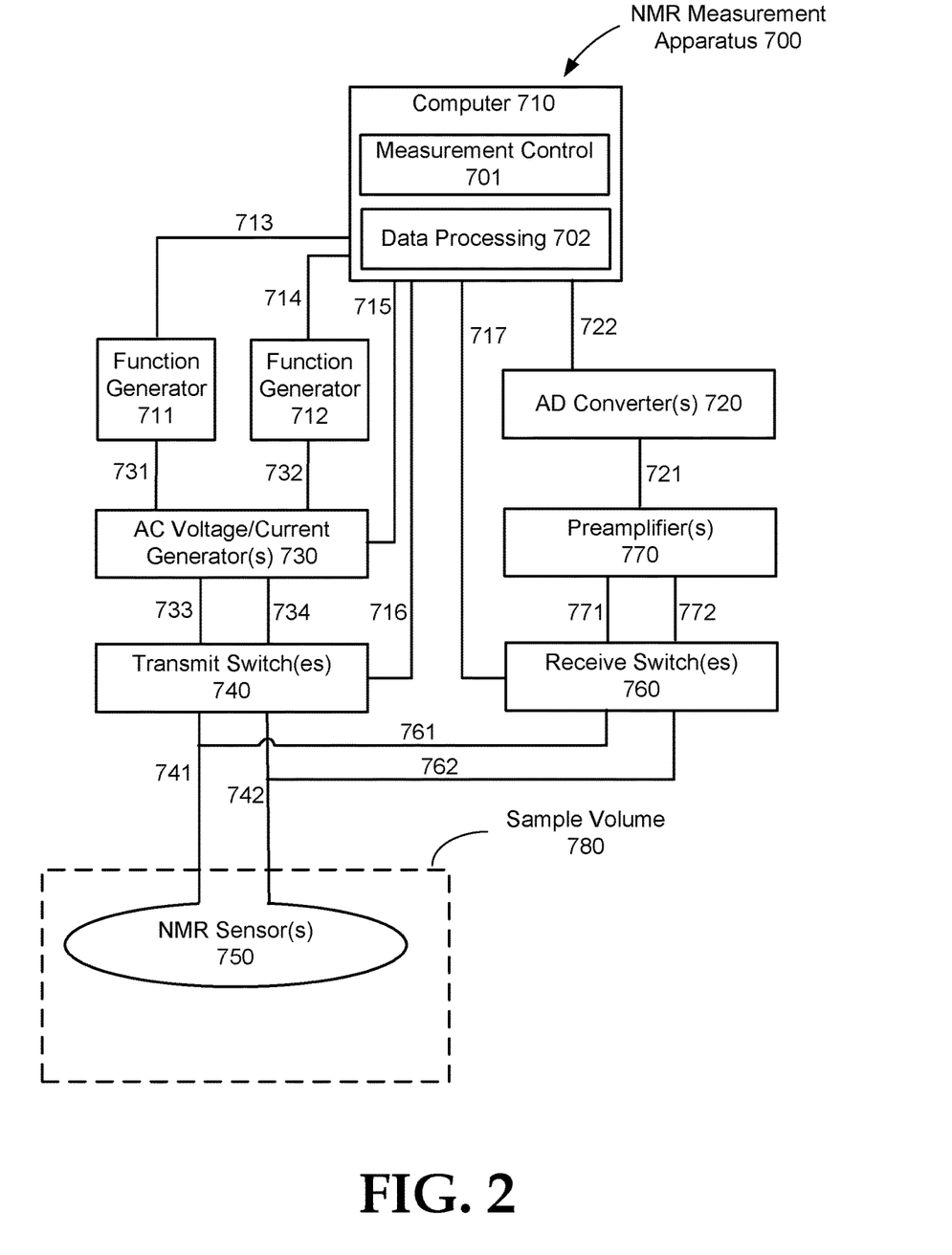
FIG. 2 depicts an example NMR measurement apparatus which may be used in connection with this disclosure.

FIG. 2 depicts an example NMR measurement apparatus such as may be used in connection with at least some aspects of this disclosure. The example NMR measurement apparatus 700 includes a computer 710, function generators 711, 712, AC voltage/current generator(s) 730, transmit switch(es) 740, NMR sensor(s) 750, receive switch(es) 760, preamplifier(s) 770, and Analog to Digital (AD) converter(s) 720. The NMR sensor(s) 750 are illustrated as an induction coil in a sample volume 780. Computer 710 comprises measurement control module(s) 701 and data processing module(s) 702.

In FIG. 2, the computer 710 is coupled to function generators 711, 712 by connections 713 and 714, respectively. The computer 710 is also coupled to AC voltage/current generator(s) 730 by connection 715, to transmit switch(es) 740 by connection 716, to receive switch(es) 760 by connection 717, and to AD converter(s) 720 by connection 722. Furthermore, function generators 711, 712 are coupled to AC voltage/current generator(s) 730 by connections 731 and 732, respectively. AC voltage/current generator(s) 730 are coupled to transmit switch(es) 740 by connections 733 and 734. Transmit switch(es) 740 are coupled to both ends 741 and 742 of the induction coil implementing NMR sensor(s) 750. The ends of the induction coil(s) 741 and 742 are coupled to receive switch(es) 760 by connections 761 and 762, respectively. Receive switch(es) 760 are coupled to preamplifier(s) 770 by connections 771 and 772. Preamplifier(s) 770 are coupled to AD converter(s) 720 by connection 721.

In general, with regard to FIG. 2, measurement control module(s) 701 may be configured to perform NMR measurements with the various other illustrated components of the NMR measurement apparatus 700. For example, the various components may be operated to produce current pulses on the NMR sensor(s) 750, to thereby create NMR excitation pulses in the sample volume 780. The computer 710 may be configured to produce a pulse by selecting a pulse phase, and activating the AC voltage/current generator(s) 730. The computer 710 may be configured to select a pulse phase for example by activating a function generator 711 or 712 corresponding to a desired pulse phase, so that the selected function generator 711 or 712 provides an input pulse phase to the AC voltage/current generator(s) 730, which is then amplified by the AC voltage/current generator(s) 730 to produce a corresponding pulse on the NMR Sensor(s) 750. The computer 710 may also optionally be configured to close one or more transmit switch(es) 740 when activating the AC voltage/current generator(s) 730, and open the transmit switch(es) 740 after activating the AC voltage/current generator(s) 730.

NMR measurement apparatus 700 may also be configured to receive and record NMR signal data received via the NMR sensor(s) 750. NMR measurement apparatus 700 may be configured to receive and record NMR signal data after one or more excitation pulses. In some embodiments, the computer 710 may be configured to close the receive switch(es) 760 after a pulse. The preamplifier(s) 770 amplify NMR signals received via induction coil(s) 750. The AD converter(s) 720 convert the received and amplified signals to digital NMR signal data, e.g. by sampling received NMR signals at a desired sampling rate, and the computer 710 or other device equipped with storage media may be configured to store the resulting digital NMR signal data.

In some embodiments, the data processing module(s) 702 may be configured to process NMR measurement data from sample volume 780, generated by operation of the measurement control module 701 and the various other components of NMR measurement apparatus 700. Data processing module(s) 702 may be configured to use measured NMR properties to determine and/or facilitate determination of any of various information used in connection with methods described herein. It will be appreciated that while the computer 710 may be configured to include data processing module(s) 702, in some embodiments NMR measurements and data processing may be performed separately, e.g., by first performing measurements with system 700, then processing acquired NMR data at a later time and/or with a different computing device or by a human operator.

It will be appreciated that NMR measurement apparatus may be configured differently than illustrated in FIG. 2 in some embodiments. To recite just a few of the many possible configuration options, computer 710 may be programmed with software that controls the generation of pulse sequences and the acquisition of data. A set of data acquisition devices may comprise devices configured generate the control signals for the pulse sequences, such as function generators 711, 712, and AD converter(s) 720 that receive, convert and/or record NMR signals. The AC voltage/current generator(s) 730 may be configured to generate one or more current pulses in the induction coil(s) 750 in a transmit mode, to induce a coherent precession of NMR spins in fluid content in the sample volume 780. Optional transmit switch(es) 740 may be configured to isolate transmitter noise from the receive circuitry during a receive mode. NMR sensor(s) 750 may be arranged other than as induction coils, and may be configured in a variety of ways as described herein or as known or as may be developed in the art. Optional receive switch(es) 760 may be configured to isolate the receive preamplifier(s) 770 from the potentially large voltage on the NMR sensor(s) 750 during transmit mode.

Optional preamplifier(s) 770 may be configured to amplify the detected NMR signals prior to digitization by the AD converter(s) 720. The optional transmit switch(es) 740 and receive switch(es) 760 may comprise active devices such as relays, and/or passive devices such as diodes. Optional tuning capacitors, not shown in FIG. 2, may be used in the transmit mode to increase the transmitted current in the induction coil(s) 750, and/or in receive mode to increase the amplitude of the NMR signal voltage across the terminals of the induction coil(s) 750.

In some embodiments, NMR sensor(s) 750 may comprise an array of coils comprising one or more transmit coils, one or more receive coils, and/or one or more combination transmit and receive coils. For example, NMR sensor(s) 750 may comprise one transmit coil and multiple receive coils. NMR sensor(s) 750 may comprise one combination transmit and receive coil, and multiple receive coils. NMR sensor(s) 750 may comprise multiple combination transmit and receive coils. These and other multicoil arrangements may be configured in some embodiments as will be appreciated. Multicoil arrangements are useful for localization of fluids in sample volume 780, as described for example in U.S. Pat. No. 7,466,128, entitled "Multicoil Data Acquisition and Processing Methods," issued Dec. 16, 2008, which is incorporated by reference herein.

Any combination of hardware and software that enables the acquisition and processing of NMR signals is suitable to implement embodiments of this disclosure. An architecture to implement the disclosed methods could comprise, for example, elements illustrated in FIG. 2, such as an AC voltage and current generator 730, a digital control system implemented at least in part by computer 710, a transmit switching circuit including transmit switch(es) 740, a receive switching circuit including receive switch(es) 760, a multi-channel receive circuit including, e.g., a plurality of induction coils in NMR sensor(s) 750, preamplifier(s) 770, a digital acquisition system including AD converter(s) 720, a digital storage device which may be implemented within computer 710 or other digital storage device, and a digital computer 710 equipped with engineering property determination software. The switching circuits may transition a system such as 700 between a transmit-mode, when the coil(s) 750 are connected to the transmit circuit, and receive-mode when the coil(s) 750 are connected to the receive circuit.

In general, NMR measurements may be collected by transmitting one or more pulses of alternating current through NMR sensor(s) 750. The alternating current may be tuned to the Larmor frequency of hydrogen nuclei, for example, and may generate a magnetic field in the sample volume 780 alternating at the Larmor frequency. The alternating magnetic field radiates into the sample volume 780 and modifies the nuclear magnetization state of hydrogen atoms present in fluids in sample volume 780. The transmitted alternating magnetic field perturbs the magnetization from equilibrium alignment in a static magnetic field, so that some component of the nuclear magnetization rotates into the transverse "xy" plane. Once rotated from equilibrium, the magnetization relaxes over time back to the equilibrium state over time, decaying from the transverse plane and re-growing along the longitudinal axis. The rotation of the magnetization by the transmitted pulse(s) and subsequent relaxation to equilibrium are described by the phenomenological Bloch equations. The evolution of the magnetization under the Bloch equations depends on several variables including the amplitude of the transmitted field, the duration and timing of the transmitted field, the phase of the transmitted field, the longitudinal relaxation time T1, FID relaxation rate T2*, and/or the spin-spin relaxation time T2 of the hydrogen nuclei under investigation. These aspects of NMR measurement may be used in determining the various NMR properties described herein.

FIG. 2 provides an example NMR measurement apparatus 700 adapted to calibrate for distortions of shapes and estimated amplitudes of recorded NMR spin or gradient echoes, in accordance with at least some embodiments of the present disclosure. The distortion may be caused by changes in a magnetic field gradient across or within a sample of investigation 750.

In FIG. 2, measurement control unit 701 may be configured to perform one or more NMR spin echo or gradient echo measurements on the sample 780 in order to record one or more NMR spin or gradient echoes. The one or more NMR spin echo or gradient echo measurements may resolve a time domain shape of the one or more recorded NMR spin or gradient echoes. Data processing unit 702 may adapted to use the one or more recorded NMR spin or gradient echoes to calculate an echo-shape calibration factor that estimates an effect of echo shape on estimated spin or gradient echo amplitude(s) of the one or more recorded NMR spin or gradient echoes, and to use the echo-shape calibration factor to correct for underestimation or overestimation of the spin or gradient echo amplitude(s). It will be appreciated that appropriate User Interface (UI) features may be displayed by computer 710, to allow a user to direct operations of the measurement control unit 701 and data processing unit 702 as appropriate for particular embodiments.

It will be appreciated that the apparatus 700 illustrated in FIG. 2 may be implemented and optionally modified to serve in a variety of different settings. For example, in some embodiments, apparatus 700 may be implemented as an NMR spectrometer, a surface NMR measurement device adapted for measurement of subsurface earth formations, an NMR logging tool adapted for deployment in an earth borehole, a medical Magnetic Resonance Imaging (MRI) device, or a device adapted for making Nuclear Quadrupole Resonance (NQR) measurements. The techniques disclosed herein are generally applicable in any NMR measurement circumstances.

Figure 3:
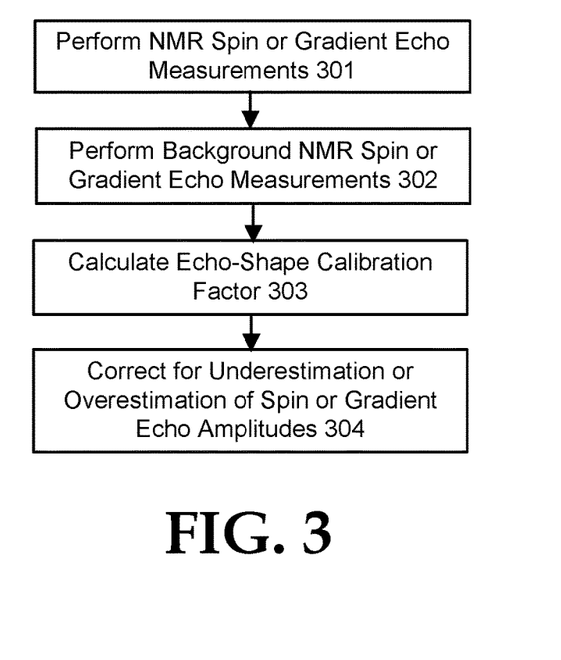
FIG. 3 illustrates an example method according to at least some embodiments of this disclosure.

FIG. 3 illustrates an example method according to at least some embodiments of this disclosure. The method of FIG. 3 may be used for calibrating for distortion of the shape and estimated amplitude of one or more NMR spin echoes, caused by changes in the magnetic field gradient across or within a sample of investigation. The methods illustrated in FIG. 3 may be carried out, for example, with a device such as illustrated in FIG. 1.

Methods according to FIG. 3 may include performing one or more NMR spin echo or gradient echo measurements 301 on a sample of interest. Data resulting from the NMR spin echo or gradient echo measurements may be recorded. The one or more NMR spin echo or gradient echo measurements may resolve a time domain shape of the one or more recorded NMR spin or gradient echoes.

In some embodiments, methods according to FIG. 3 may include performing one or more optional background NMR spin echo or gradient echo measurements 302 on a known sample under a background magnetic field gradient condition to resolve a time domain shape of one or more recorded background NMR spin or gradient echoes. The one or more recorded background NMR spin or gradient echoes may be normalized to have a first unit peak amplitude, and the one or more recorded NMR spin or gradient echoes, recorded pursuant to the one or more NMR spin echo or gradient echo measurements on the sample, may be normalized to have a second unit peak amplitude. The one or more recorded NMR spin or gradient echoes may be used to calculate the echo-shape calibration factor by calculating the echo-shape calibration factor as a ratio of a time-windowed average of the one or more normalized background NMR spin or gradient echo measurements, divided by a time-windowed average of the one or more normalized NMR spin echo or gradient echo measurements.

Methods according to FIG. 3 may include using the one or more recorded NMR spin or gradient echoes to calculate an echo-shape calibration factor 303. The echo-shape calibration factor may estimate an effect of echo shape on estimated spin or gradient echo amplitude(s) of the one or more recorded NMR spin or gradient echoes. The echo-shape calibration factor may be used to correct for underestimation or overestimation of the spin or gradient echo amplitude(s) 304. The echo-shape calibration factor may be calculated, for example, as a ratio of a peak measured or estimated amplitude of a spin or gradient echo in the one or more NMR spin or gradient echo measurements, divided by a time-windowed average of the spin or gradient echo within a time-averaging window. Using the echo-shape calibration factor to correct for the underestimation or overestimation of the spin or gradient echo amplitude(s) may comprise, for example, multiplying the spin or gradient echo amplitude(s) by the echo-shape calibration factor.

In some embodiments, spin or gradient echo shape(s) in the one or more recorded NMR spin or gradient echoes may be estimated at least in part by averaging multiple time-offset spin or gradient echoes, in order to reduce noise.

In some embodiments, e.g., for fluid-saturated samples investigated using an NMR spectrometer, methods may correct for NMR spin or gradient shape variations on fluid content measurements. When the sample comprises an earth core sample or a soil sample, and measurements are performed with a NMR spectrometer, and methods may include performing one or more background calibration measurements in the NMR spectrometer, using samples of bulk fluids.

In some embodiments, the one or more NMR spin or gradient echo measurements may be performed within an earth borehole with an NMR logging tool, and methods may include performing one or more background calibration measurements using the NMR logging tool (or a similar NMR logging tool) to measure an NMR response of bulk fluids.

In some embodiments, the one or more NMR spin or gradient echo measurements may be performed with an earth's field surface NMR instrument, and the spin or gradient echo amplitude(s) corrected using the echo shape calibration factor may comprise spin or gradient echo amplitude(s) used for water content and relaxation time estimates. In some embodiments, the one or more NMR spin echo or gradient echo measurements comprise a Nuclear Quadrupole Resonance (NQR) measurement.

In some embodiments, methods according to FIG. 3 may apply the echo-shape calibration factor to the one or more recorded NMR spin or gradient echoes to correct for errors in estimated echo amplitudes due to unknown external or internal magnetic field gradients across the sample.

In some embodiments, the one or more recorded NMR spin or gradient echoes may be induced and measured, e.g., at block 301, between NMR measurements of bulk fluids and NMR measurements of fluid-saturated porous materials. Using the one or more recorded NMR spin or gradient echoes to calculate the echo-shape calibration factor at block 303 may use different spin or gradient echo shapes induced and measured between the NMR measurements of bulk fluids and the NMR measurements of fluid-saturated porous materials.

In some embodiments, using the one or more recorded NMR spin or gradient echoes may be used to calculate the echo-shape calibration factor at block 303 may comprise calculating an effect of magnetically susceptible earth formations on NMR estimates of volumetric fluid content within said earth formations. In general, the one or more recorded NMR spin or gradient echoes, or the echo shape calibration factor, or a combination thereof, may be used to determine magnetic susceptibility effects in the sample. The measurements may be performed with a medical Magnetic Resonance Imaging (MRI) device, and methods may determine magnetic susceptibility effects in medical samples (e.g., human organs and the like). The measurements may be performed within an earth borehole with an NMR logging tool, or at an earth surface with an earth's field surface NMR instrument, and methods may determine magnetic susceptibility effects in subsurface earth formations. The measurements may be performed within a NMR spectrometer, and methods may determine magnetic susceptibility effects in corresponding spectrometer samples. The measurements may comprise Nuclear Quadrupole Resonance (NQR) measurements, and methods may determine magnetic susceptibility effects in samples measured by NQR.

There are various approaches by which apparatus and methods processes described herein can be implemented (e.g., hardware, software, and/or firmware), and the preferred approach may vary with the context in which the apparatus and methods are deployed. For example, if an implementer determines that speed and accuracy are paramount for operations of a computer or controller, the implementer may opt for a mainly hardware and/or firmware vehicle; if flexibility is paramount, the implementer may opt for a mainly software implementation; or, yet again alternatively, the implementer may opt for some combination of hardware, software, and/or firmware.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

While various embodiments have been disclosed herein, other aspects and embodiments will be apparent to those skilled in art.

The invention claimed is:

1. A method for calibrating for distortion of a shape and estimated amplitude of one or more recorded Nuclear Magnetic Resonance (NMR) spin or gradient echoes, the distortion caused by changes in a magnetic field gradient across or within a sample of investigation, comprising:
    performing one or more background NMR spin or gradient echo measurements on a known sample under a background magnetic field gradient condition;
    performing one or more NMR spin or gradient echo measurements on the sample in order to record one or more NMR spin or gradient echoes, wherein the one or more NMR spin or gradient echo measurements resolve a time domain shape of the one or more recorded NMR spin or gradient echoes;
    using the one or more recorded NMR spin or gradient echoes to calculate an echo-shape calibration factor that estimates an effect of echo shape on estimated spin or gradient echo amplitude(s) of the one or more recorded NMR spin or gradient echoes, wherein calculating the echo-shape calibration factor comprises calculating a ratio of the one or more background NMR spin or gradient echo measurements to the one or more NMR spin or gradient echo measurements; and
    using the echo-shape calibration factor to correct for underestimation or overestimation of the spin or gradient echo amplitude(s).

2. The method of claim 1, wherein the echo-shape calibration factor is calculated as a ratio of a peak measured or estimated amplitude of a spin or gradient echo in the one or more NMR spin or gradient echo measurements, divided by a time-windowed average of the spin or gradient echo within a time-averaging window.

3. The method of claim 1, wherein using the echo-shape calibration factor to correct for the underestimation or overestimation of the spin or gradient echo amplitude(s) comprises multiplying the spin or gradient echo amplitude(s) by the echo-shape calibration factor.

4. The method of claim 1, further comprising resolving a time domain shape of one or more recorded background NMR spin or gradient echoes.

5. The method of claim 4, further comprising normalizing the one or more recorded background NMR spin or gradient echoes to have a first unit peak amplitude, and normalizing the one or more recorded NMR spin or gradient echoes, recorded pursuant to the one or more NMR spin or gradient echo measurements on the sample, to have a second unit peak amplitude.

6. The method of claim 5, wherein the ratio of the one or more background NMR spin or gradient echo measurements to the one or more NMR spin or gradient echo measurements comprises a ratio of a time-windowed average of the one or more normalized background NMR spin or gradient echo measurements, divided by a time-windowed average of the one or more normalized NMR spin or gradient echo measurements.

7. The method of claim 1, further comprising applying the echo-shape calibration factor to the one or more recorded NMR spin or gradient echoes to correct for errors in estimated echo amplitudes due to unknown external or internal magnetic field gradients across the sample.

8. The method of claim 1, further comprising estimating spin or gradient echo shape(s) in the one or more recorded NMR spin or gradient echoes at least in part by averaging multiple time-offset spin or gradient echoes in order to reduce noise.

9. The method of claim 1, further comprising correcting for NMR spin or gradient shape variations on fluid content measurements of fluid-saturated samples investigated using an NMR spectrometer.

10. The method of claim 1, wherein the one or more recorded NMR spin or gradient echoes are induced and measured between NMR measurements of bulk fluids and NMR measurements of fluid-saturated porous materials, and wherein using the one or more recorded NMR spin or gradient echoes to calculate the echo-shape calibration factor uses different spin or gradient echo shapes induced and measured between the NMR measurements of bulk fluids and the NMR measurements of fluid-saturated porous materials.

11. The method of claim 1, wherein using the one or more recorded NMR spin or gradient echoes to calculate the echo-shape calibration factor comprises calculating an effect of magnetically susceptible earth formations on NMR estimates of volumetric fluid content within said earth formations.

12. The method of claim 1, wherein the sample comprises an earth core sample or a soil sample, wherein the one or more NMR spin or gradient echo measurements are performed with a NMR spectrometer, and further comprising performing one or more background calibration measurements in the NMR spectrometer, using samples of bulk fluids.

13. The method of claim 1, wherein the one or more NMR spin or gradient echo measurements are performed within an earth borehole with an NMR logging tool, and further comprising performing one or more background calibration measurements using the NMR logging tool or a similar NMR logging tool to measure an NMR response of bulk fluids.

14. The method of claim 1, wherein the one or more NMR spin or gradient echo measurements are performed with an earth's field surface NMR instrument, and wherein the spin or gradient echo amplitude(s) corrected using the echo shape calibration factor comprise spin or gradient echo amplitude(s) used for water content and relaxation time estimates.

15. The method of claim 1, further comprising using the one or more recorded NMR spin or gradient echoes or the echo shape calibration factor to determine magnetic susceptibility effects in the sample.

16. The method of claim 15, wherein the one or more NMR spin or gradient echo measurements are performed with a medical Magnetic Resonance Imaging (MRI) device.

17. The method of claim 15, wherein the one or more NMR spin or gradient echo measurements are performed within an earth borehole with an NMR logging tool, or at an earth surface with an earth's field surface NMR instrument.

18. The method of claim 15, wherein the one or more NMR spin or gradient echo measurements are performed with a NMR spectrometer.

19. An apparatus adapted to calibrate for distortions of shapes and estimated amplitudes of recorded NMR spin or gradient echoes, the distortion caused by changes in a magnetic field gradient across or within a sample of investigation, the apparatus comprising:
 a measurement control unit configured to perform one or more NMR spin or gradient echo measurements on the sample in order to record the one or more NMR spin or gradient echoes, wherein the one or more NMR spin or gradient echo measurements resolve a time domain shape of the one or more recorded NMR spin or gradient echoes; and
 a data processing unit adapted to:
  use the one or more recorded NMR spin or gradient echoes and one or more background NMR spin or gradient echo measurements to calculate an echo-shape calibration factor that estimates an effect of echo shape on estimated spin or gradient echo amplitude(s) of the one or more recorded NMR spin or gradient echoes, wherein the echo-shape calibration factor is calculated as a ratio of the one or more background NMR spin or gradient echo measurements to the one or more NMR spin or gradient echo measurements; and
  use the echo-shape calibration factor to correct for underestimation or overestimation of the spin or gradient echo amplitude(s).

20. A method for calibrating for distortion of a shape and estimated amplitude of one or more recorded Nuclear Magnetic Resonance (NMR) spin or gradient echoes, the distortion caused by changes in a magnetic field gradient across or within a sample of investigation, comprising:
 performing one or more NMR spin or gradient echo measurements on the sample in order to record one or more NMR spin or gradient echoes, wherein the one or more NMR spin or gradient echo measurements resolve a time domain shape of the one or more recorded NMR spin or gradient echoes, and wherein the one or more NMR spin or gradient echoes are induced and measured between NMR measurements of bulk fluids and NMR measurements of fluid-saturated porous materials;
 using the one or more recorded NMR spin or gradient echoes to calculate an echo-shape calibration factor that estimates an effect of echo shape on estimated spin or gradient echo amplitude(s) of the one or more recorded NMR spin or gradient echoes, wherein calculating the echo-shape calibration factor comprises calculating a ratio of a peak measured or estimated amplitude of a spin or gradient echo in the one or more NMR spin or gradient echo measurements, divided by a time-windowed average of the spin or gradient echo within a time-averaging window; and using the echo-shape calibration factor to correct for underestimation or overestimation of the spin or gradient echo amplitude(s).

* * * * *